United States Patent [19]

Marks

[11] Patent Number: 4,784,153

[45] Date of Patent: Nov. 15, 1988

[54] METHOD OF AND APPARATUS FOR DETECTING CARDIAC RHYTHM DISTURBANCE

[76] Inventor: Lloyd A. Marks, 727 Great Springs Rd., Bryn Mawr, Pa. 19010

[21] Appl. No.: 929,414

[22] Filed: Nov. 12, 1986

[51] Int. Cl.⁴ ............................................... A61B 5/04
[52] U.S. Cl. ..................................... 128/701; 128/704; 128/696; 128/702; 128/703; 128/708
[58] Field of Search ............... 128/701, 690, 696, 702, 128/703, 704

[56] References Cited

U.S. PATENT DOCUMENTS

| | | | |
|---|---|---|---|
| 3,565,058 | 2/1971 | Mansfield | 128/701 |
| 3,650,264 | 3/1972 | Janssen | 128/701 |
| 3,732,868 | 5/1973 | Willems et al. | 128/701 |
| 3,760,100 | 9/1973 | Ragsdale et al. | 128/701 |
| 3,830,227 | 8/1974 | Green | 128/701 |
| 3,841,315 | 10/1974 | Kopp | 128/701 |
| 3,861,387 | 1/1975 | Lawhorn et al. | 128/701 |
| 4,120,296 | 10/1978 | Prinz | 128/690 |
| 4,181,134 | 1/1980 | Mason et al. | 128/690 |
| 4,181,135 | 1/1980 | Andresen et al. | 128/702 |
| 4,409,983 | 10/1983 | Albert | 128/690 |
| 4,425,921 | 1/1984 | Fujisaki et al. | 128/690 |
| 4,467,813 | 8/1984 | Schomburg | 128/702 |
| 4,576,178 | 3/1986 | Johnson | 128/701 |
| 4,598,281 | 7/1986 | Maas | 128/696 |

Primary Examiner—William E. Kamm
Assistant Examiner—Timothy J. Keegan
Attorney, Agent, or Firm—Wigman & Cohen

[57] ABSTRACT

A method for generating audio information to indicate the presence and nature of a cardiac rhythm disturbance is disclosed. More specifically, this method produces sounds which accompany atrial and ventricular ectopic rhythms, allowing the physician to appreciate the presence of such rhythms without having to visually inspect the morphology of the electrocardiogram signal. Furthermore, the sounds differ according to the type of ectopic rhythm present. This method provides such information in real time, allowing the physician to correlate the information with the current condition of the patient. The electrocardiogram signal is analyzed by a microprocessor or microcomputer which in turn controls a tone generator to produce the audio output.

17 Claims, 5 Drawing Sheets

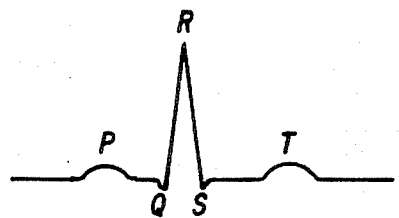
FIG. 1
NORMAL P-QRS-T COMPLEX
FIG. 2
CONDUCTION SYSTEM OF THE HEART
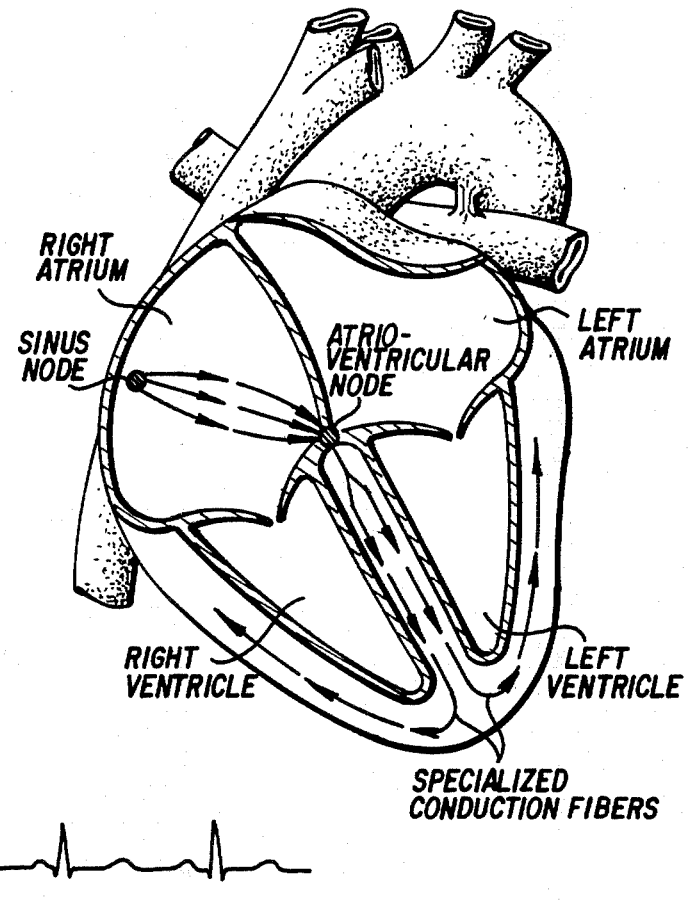
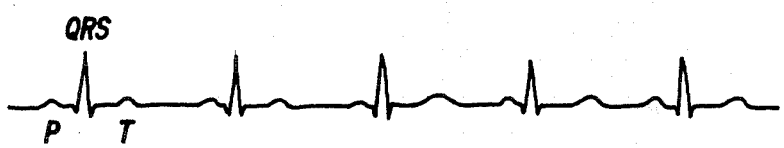
FIG. 3
NORMAL SINUS RHYTHM
FIG. 4
PREMATURE ATRIAL CONTRACTIONS
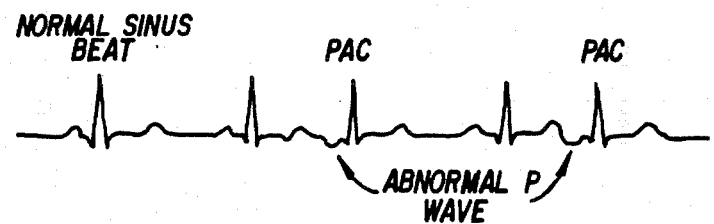
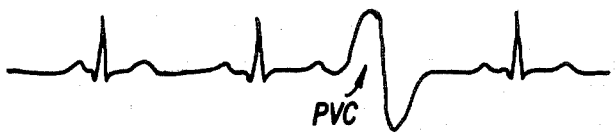
FIG. 5
PREMATURE VENTRICULAR CONTRACTIONS

MULTIPLE UNIFOCAL PREMATURE VENTRICULAR CONTRACTIONS

BIGEMINY (UNIFOCAL)

TRIGEMINI (UNIFOCAL)

COUPLET

VENTRICULAR TACHYCARDIA

MULTIFORM PREMATURE VENTRICULAR CONTRACTIONS

MULTIFORM BIGEMINI

MULTIFORM VENTRICULAR TACHYCARDIA

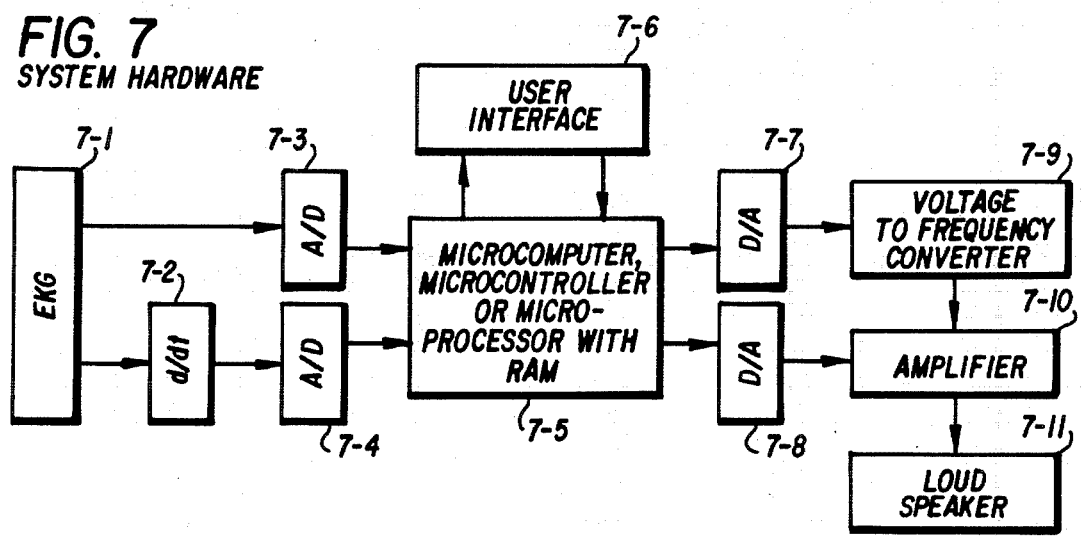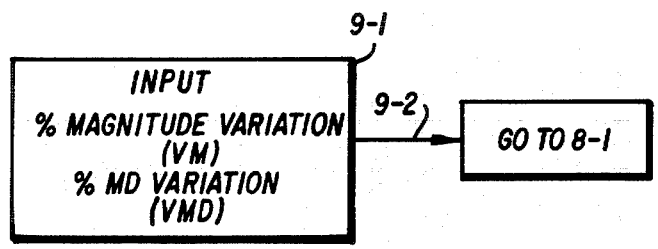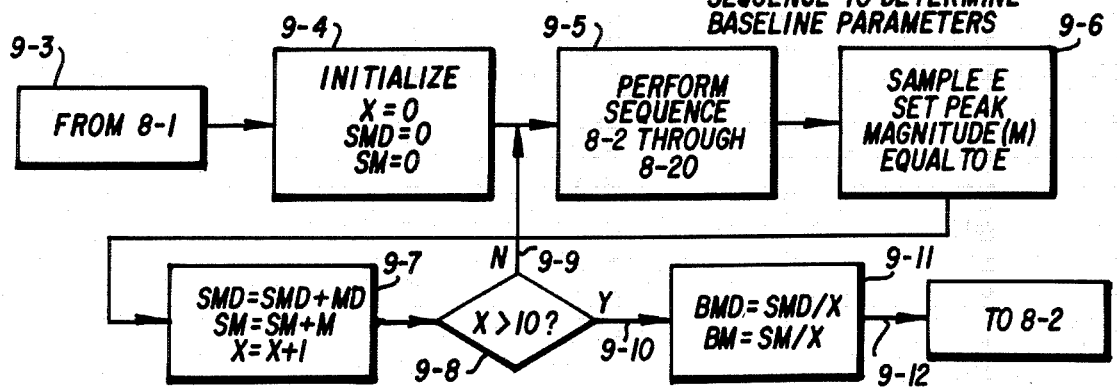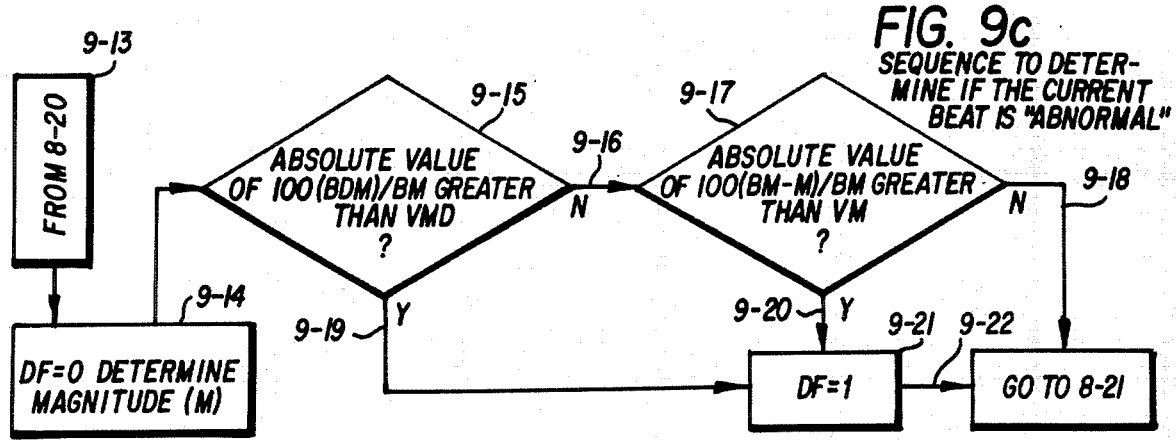

SOFTWARE FLOWCHART FOR
EMBODIMENT No. 1

SEQUENCE TO SUPRESS SOUND PRODUCTION OF "NORMAL" BEATS

THE EKG SIGNAL MODULATES THE FREQUENCY OF THE OUTPUT TONE AND THE NOTCH FILTER ONLY PRODUCES A SIGNAL WHICH DEPARTS FROM THE BASELINE.

METHOD OF AND APPARATUS FOR DETECTING CARDIAC RHYTHM DISTURBANCE

BACKGROUND OF THE INVENTION

Every time the heart beats, electrical activity is generated. This activity, called the electrocardiogram (EKG) is the result of cellular depolarization which in turn causes the cardiac muscle cells to contract. The EKG signal from a single cardiac cycle is shown in FIG. 1. It consists of a P wave, which results from depolarization of the atria (upper receiving chambers of the heart), a QRS complex, which results from the normal, coordinated, depolarization of the ventricles (lower, thick, muscular pumping chambers), and a T wave, which is caused by ventricular repolarization. Depolarization originates in specific atrial tissue called the "sinus node", passes through the atria, then through specific junctional tissue between the atria and ventricles called the "atrioventricular node" (FIG. 2). The signal then passes through specialized conduction tissue which delivers the depolarization activity to both the left and right ventricles simultaneously. This results in a narrow QRS complex, usually less than 10 msec in duration. If the pacemaker "fires" regularly, this results in "normal sinus rhythm". Such a normal rhythm is shown in FIG. 3.

Any variation from normal sinus rhythm may be broadly referred to as an "arrhythmia". For example, if atrial tissue other than the sinus node spontaneously depolarizes and initiates a cardiac contraction, a "premature atrial contraction" (PAC) will result producing a characteristic change in the EKG (FIG. 4). Note that the P waves in the premature beats occur early and are shaped differently than the sinus P waves, as they have originated from a different "ectopic" location. As a general rule, these PAC's do not have serious clinical consequences.

PAC's have normal QRS morphology, as the derangement (abnormality or ectopic beat) has occurred entirely above the ventricles. By contrast, ventricular ectopic beats radically alter the shape of the QRS complex (FIG. 5). This is due to the fact that when depolarization originates from an ectopic ventricular focus, the electrical activity does not pass through the specialized conduction tissue, and arrives at the two ventricles spread out over time. Thus, such complexes are generally broad and slurred as shown.

A single premature ventricular contraction (PVC) is generally not of clinical significance. However, if many such beats occur together, they may compromise cardiac function. Furthermore, if many PVC's are occurring from many different sites in the ventricle (multifocal PVC's) this may indicate a serious global derangement of ventricular activity which may constitute a medical emergency. A number of important arrhythmias and their corresponding EKG patterns will be briefly described.

FIG. 6a shows multiple unifocal PVC's. Note that the shapes of the ectopic beats are uniform. When such beats occur in a regular pattern they may be referred to with specific terminology. For example, "bigeminy" is when every other beat is abnormal (FIG. 6b). "Trigeminy" is when every third beat is abnormal (FIG. 6c). When two such beats occur in a row it is called a "couplet" (FIG. 6d). When they occur three or more in a row they are referred to as "a run of ventricular tachycardia" (FIG. 6e).

When PVC's originate from more than one location, they are called "multifocal" and the corresponding EKG has abnormal complexes which differ from one another. Such "multiform" PVC's are shown in FIG. 6f. If every other beat is a multiform PVC this results in "multiform bigeminy" (FIG. 6g). If multiform PVC's occur one after another, this constitutes a "run of multiform ventricular tachycardia" (FIG. 6h).

Each of these rhythm disturbances has its own clinical significance. Therefore, it is important for the physician to identify and categorize the arrhythmia. Currently, this is done by providing the physician with a graphic representation of the EKG tracing which he or she may analyze. Such tracings can be either provided as hard copy or made available as a stored tracing on a monitor screen. It is also common to record the EKG signal for 24 hours and provide the physician with excerpts from such a stored waveform for detailed analysis. This is referred to as a "holter monitor recording."

There are obviously situations in which it is desirable to execute such rhythm analysis immediately. Furthermore, there are environments, most notably during cardiac catheterization procedures, when it is not convenient for the physician to constantly look at a monitor. Thus, it would be desirable to provide useful information about these arrhythmias to the physician by a distinct audible signal, whereby the nature of the signal not only indicates the presence of an arrhythmia, but also provides information about the type of arrhythmia.

Automated devices have been developed to identify PVC's as well as to analyze and categorize the shape of such beats. Some of these systems apply to analysis of 24 hour "holter cardiogram" recordings, and thus do not function in real time (e.g., U.S. Pat. No. 4,316,249 to Gallant et al). Some categorize PVC's in real time and store them digitally for later analysis. One device identifies and categorizes different types of ventricular arrhythmias in real time, but does not provide an audio output to alert the physician of specific, abnormal ventricular beats (U.S. Pat. No. 4,589,420 to Adams et al). Other devices identify abnormal ventricular beats with an audible alarm, but do not provide varying outputs that reflect different types of PVC's (e.g., U.S. Pat. Nos. 4,115,864 to Vick et al; 3,881,467 to Stanley et al; 3,861,387 to Lawhorn et al). Still other devices perform an analysis of the EKG in real time, but do not provide audible alarms to alert the physician as to the results of such analysis (e.g., U.S. Pat. Nos. 4,193,393 to Schlager and 4,023,564 to Valiquette et al). Also, one device (Cardio-Beeper) produces a continuous tone whose frequency is modulated by the amplitude of the EKG waveform for transmission of an EKG over telephone. The sound emanating from this device is characteristic of the morphology of the EKG on a continuous basis, but because it produces a continuous whining sound with varying pitch, it is difficult to listen to and is not suitable for monitoring applications.

The device disclosed in this application remedies such deficiencies by providing audible output with each beat which both identifies and characterizes rhythm disturbance, thus helping the physician to become aware of both the occurrence and the nature of the arrhythmia.

OBJECTS AND SUMMARY OF THE INVENTION

From the above discussion, it should be apparent that there exists a need for a method and/or device which can provide audible information to a physician about the changes in EKG morphology which characterize different types of arrhythmias. Furthermore, the method should provide an output which is suitable for use in patient care situations where a physician's visual attention may be otherwise occupied, such as the cardiac catherization laboratory.

It is, therefore, a primary object of this invention to provide an audible monitor apparatus which generates sounds which characterize changes in rhythm and changes in the morphology of the EKG signal.

More specifically, it is an object of the invention to provide audible output occurring with each cardiac cycle which is determined by characteristics of each QRS complex.

Furthermore, it is an object of this invention to provide such output in real time, making the information available for immediate clinical use.

Furthermore, it is an object of this invention to provide optional identification of abnormal beats from normal beats characterized during a baseline characterization procedure.

Furthermore, it is an object of this invention to provide an embodiment which characterizes the QRS complex by measuring various parameters which characterize its shape and modifies the pitch of the output tone as a function of such parameters.

Furthermore, it is an object of this invention to provide an embodiment which characterizes the QRS complex by its rate of upstroke and modifies the pitch of the output tone as a function of such upstroke rate.

Furthermore, it is an object of this invention to provide an embodiment which characterizes the QRS complex by its rate of upstroke and/or its peak magnitude and modifies the pitch of the output tone as a function of such upstroke rate and/or peak magnitude.

Furthermore, it is an object of this invention to provide a means to enable the tone at either the point of identification of a QRS complex or at the peak of the QRS complex and to maintain that tone until the EKG signal returns to baseline.

Furthermore, it is an object of this invention to provide an embodiment in which the tone output is enabled whenever QRS complex is identified, the tone produced is frequency modulated by the amplitude of the EKG signal or its first derivation, and the tone is disabled when the EKG signal returns to the baseline.

Furthermore, it is an object of this invention to provide an embodiment as in the above paragraph, but in which only abnormal complexes enable the production of the modulated tone and normal complexes are either silent or accompanied by a distinctly different (e.g., high pitched and short duration) tone.

Furthermore, it is an object of this invention to provide audible output which will allow a physician to distinguish between PAC's, uniform PVC's, multiform PVC's, bigeminy, trigeminy, couplets, ventricular tachycardia and other arrhythmias.

Furthermore, it is an object of this invention to provide these functions with a microcomputer or microprocessor based system.

Furthermore, it is an object of this invention to provide these functions using an EKG input which can be easily derived from standard EKG monitoring devices and thus may be "piggybacked" on such a device without making direct patient contact.

Furthermore, it is an object of this invention to provide these functions with a device which can be portable and batter operated.

These objects are provided by a method in which an EKG signal (and preferably its first derivative also) are provided to a microcomputer or microprocessor in real time by use of an analog to digital converter. In one embodiment, the signal is continuously analyzed for rapid deflections which indicate that a QRS complex has occurred. After identification of the QRS complex, repeated measurements of the rate of change (first derivative) are executed (either directly if the signal is available from the output of an analog differentiator or computed digitally from the EKG input) and these values are stored. When the peak of the deflection occurs (as indicated by a rapid change in the sign of the first derivative), the magnitude of this point is measured and stored. Also, the stored values of the first derivative are used to compute an average value of the first derivative during the sampling interval. Then, a tone with a frequency determined by a mathematical relationship to the aforementioned stored values of the first derivative and/or peak magnitude is enabled. This tone is maintained until the EKG signal returns to and stays at the baseline value for a predetermined minimum time.

Other stated objects of the invention are provided by an apparatus or method in which these values of first derivative by peak magnitude are measured in baseline "normal" beats. Subsequent beats are then compared to these baseline beats. When they differ from the baseline beats by a significant amount an abnormal beat is identified. An abnormal beat is determined in the algorithm by a sensitivity range dictated by user input. Once such identification occurs, the system user may be alerted by a number of methods. For example, a light could flash with each abnormal beat. Alternatively, or in addition, the tone could be disabled for "normal" beats, or a distinctly different tone could be provided for the "normal" beats.

Other stated objects of the invention are provided by an apparatus or method in which the identification of an abnormal beat enables a tone which is frequency modulated by the amplitude of the EKG signal (or a signal uniquely derived from the EKG signal, such as its first derivative) and the tone is disabled when the EKG signal (or its first derivative) returns to baseline for a prescribed period of time.

The method of this invention provides an improved way to monitor patients with rhythm disturbances, particularly when it is not convenient for the physician to constantly observe a video monitor.

BRIEF DESCRIPTION OF THE DRAWINGS

FIG. 1 is a diagram of a normal isolated P-QRS-T complex

FIG. 2 is a diagram of the electrical conduction system of the heart.

FIG. 3 is a tracing of normal sinus rhythm.

FIG. 4 is a tracing of premature atrial contractions.

FIG. 5 is a tracing of premature ventricular contraction.

FIG. 6 is a series of ventricular arrhythmias.

FIG. 7 is a schematic diagram of the system
FIG. 9 is a flowchart of the software modifications in the second embodiment.
FIG. 9a is a flowchart of the sequence for input of parameters which determine how much variation from baseline is necessary to define an "abnormal" beat.
FIG. 9b is a flowchart of the sequence to determine baseline parameters.
FIG. 9c is a flowchart of the sequence to determine if the current beat is "abnormal".

DETAILED DESCRIPTION OF THE INVENTION

Figure 6A:
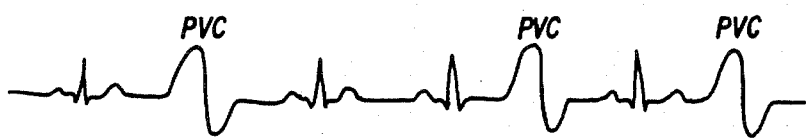
FIG. 6a is a tracing of multiple unifocal premature ventricular contractions.
Figure 6B:
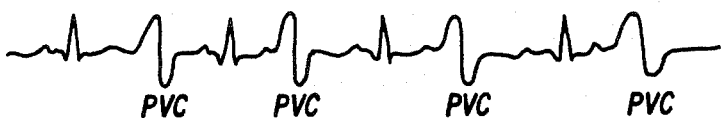
FIG. 6b is a tracing of bigeminy.
Figure 6C:
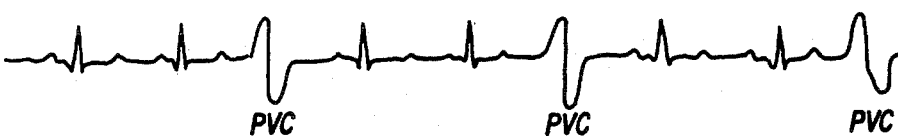
FIG. 6c is a tracing of trigeminy.
Figure 6D:
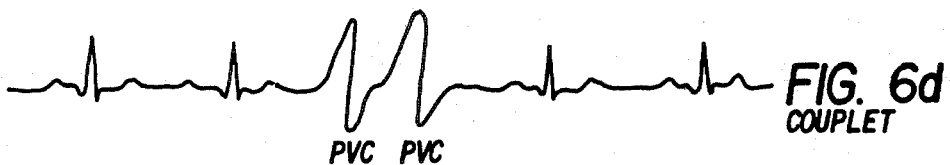
FIG. 6d is a tracing of couplet.
Figure 6E:
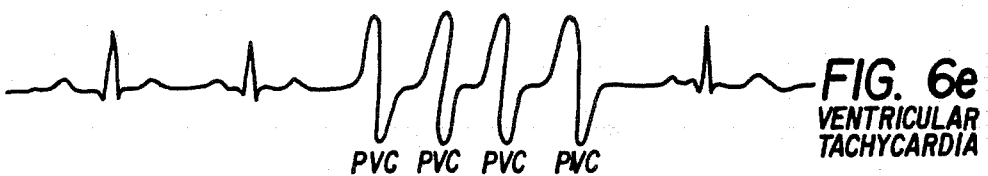
FIG. 6e is a tracing of ventricular tachycardia.
Figure 6F:
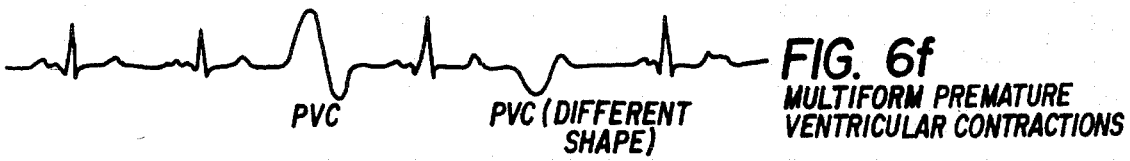
FIG. 6f is a tracing of multiform premature ventricular contractions.
Figure 6G:
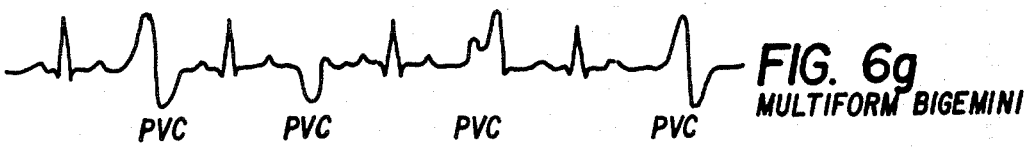
FIG. 6g is a tracing of multiform bigeminy.
Figure 6H:
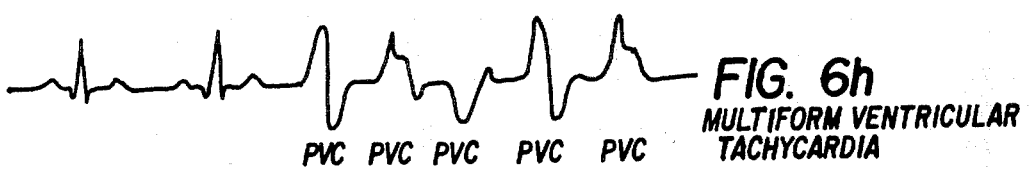
FIG. 6h is a tracing of multiform ventricular tachycardia.

In the first embodiment, the system does not distinguish between normal and abnormal beats through the use of the computerized algorithm, but rather produces a sound for each and every beat detected and allows the physician to distinguish between such normal and abnormal beats on the basis of the different sounds which they produce. The hardware of the first embodiment is shown in FIG. 7.

Referring to FIG. 7, the EKG signal (7-1) is derived from a conventional source such as an Abbot EK50 EKG module. The signal is then passed through an analog differentiation circuit (7-2). The EKG signal and its first derivative are then passed respectively through channels 7-3 and 7-4 of an analog to digital converter which makes the signal available to a computing means such as a microcomputer (such as an Apple II) or a microcontroller (such as an Intel 8748H) or a microprocessor (such as an Intel 8088) with accessory random access memory (7-5). It will be clear to one skilled in the art that these are equivalent hardware approaches. By example, an application with a microcomputer is discussed below.

If an Apple II computer is used, the analog to digital function may be performed by a Mountain Computer A/D-D/A converter. The microcomputer (or alternate device) is connected to a user interface (7-6) which may be a keyboard, series of pushbuttons, potentiometers, or combinations of these input devices. Selected outputs of the microcomputer are made available for tone generation through channels 7-7 and 7-8 of a digital to analog converter. This function may also be performed by the Mountain Computer A/D-D/A converter. The output of channel 7-7 provides a voltage signal which sets the pitch produced by a voltage to frequency converter (7-9). The output of 7-9 is then amplified by an amplifier circuit (7-10), which is enabled and disabled by the output from channel 7-8. The output of the amplifier is used to drive a loudspeaker (7-11). Analog differentiator, voltage to frequency converter and amplifier circuits are well known to those skilled in the art.

It will be apparent to one skilled in the art that if a microcomputer is used as the computing means, the microcomputer may be used to generate the sound without requiring the use of an external voltage to frequency converter, amplifier or loudspeaker.

An algorithm to implement the first embodiment is now discussed. The algorithm is started by requesting information from the user (8-1). The parameters requested are input sensitivity (S), tone modifier (T), and baseline determination sensitivity (B). Alternatively, these parameters could be provided with default values gleaned from experience and programmed into the algorithm or they could be varied by changing the position of a resistive-type device, the position of which could be determined by the computer. Then (8-2) flag F, counter N, sum of D (SD), and the enable tone flag (ET) are initialized to zero. For the purpose of this discussion, the digitized EKG input is referred to as E and d(EKG)/dt is referred to as D. D is sampled and tested to see if it exceeds S (8-3), thus indicating that a deflection of sufficient magnitude has been detected. If D does not exceed S, then (8-4), after a waiting period of approximately 5 msec, control returns to 8-3 and a new sample is taken. If D is greater than S (8-5), then, after waiting approximately 5 msec (8-6), D is once again tested to see if it is greater than S (8-7). If it is not, control returns to 8-3. If the condition of D greater than S is confirmed for the second time (8-9), then a QRS complex is identified. It is important to note that this is only one of many ways to identify a QRS complex and that many schemes may exist for making such a determination.

Once a QRS complex is identified, control then passes to 8-10, where D is sampled, added to SD, and the counter N is incremented. Then, N is tested to see if it is greater than 1 (8-11). If it is not (8-12), control passes back to 8-10. If it is (8-13), control passes to B-14 where the sign of D(N) is compared to the sign of D(N−1). If a sign change has occurred (8-15), flag F is set to 1 (8-16), and control returns to 8-10. If a sign change has not occurred, then control passes to 8-17 where the flag is tested. If the flag is not set (8-18), control returns to 8-10. If the flag is set (8-19), this indicates that a sign change took place and was maintained for the next sample. This indicates that the peak of the QRS deflection has occurred and control passes to 8-20 where the mean of D (MD) is computed as MD=SD/N. At this point, the peak magnitude (M) of the QRS complex could be determined as the current value of the EKG signal. Now, the output tone can be generated with its pitch determined mathematically from MD and/or M.

Once MD is computed, control passes to 8-21, where the output frequency (FREQ) is determined as FREQ=2 KHz+(T * MD). Alternatively, M could be substituted for MD or FREQ could be determined by a mathematical combination of the two parameters MD and M. Of course, the 2 KHz value may be modified. FREQ will be made available to the tone generator as described before through channel 7-7 of the D/A converter. After FREQ is determined, control passes to 8-22, where a tone enable signal is generated by setting ET=1 and made available to D/A channel 7-8. Then (8-23) the flag and counter are reset to zero. The next sequence (8-24 through 8-36) is an algorithm to determine when the QRS complex has terminated so that the tone may be disabled. In 8-24, the EKG signal is sampled as E(N), and N is incremented by one. After waiting approximately 5 msec (8-25), N is tested to see if it is greater than one. If it is not (8-27), control returns to 8-24. If it is (8-28), control passes to 8-29 where it is determined if a significant change in the signal has occurred from the prior sample. This is done by determining if the absolute value of E(N)−E(N−1) is greater than B. If it is not (8-30), control passes back to 8-24. If it is (8-31), the flag is tested (8-32) to see if it has already been set. If not (8-33), the flag is set (8-34) and control passes back to 8-24 for another sample. If the flag is already set (8-35), then it has been determined that the signal has returned to baseline and the tone is disabled (8-36) by setting ET back to zero. Then, control passes back (8-37) to 8-2, so that the sequence may be repeated for the next cardiac cycle.

A second embodiment of the invention will now be discussed. This embodiment includes the feature of embodiment #1, but in addition, includes software which distinguishes normal beats from abnormal beats. In this embodiment, if a beat is identified as "normal", sound generation is suppressed. Thus, tones will only be generated for "abnormal" QRS complexes. However, it will be evident to one skilled in the art, that once this determination is made, it could be put to other uses, such as flashing a light for abnormal beats, or generating a distinctly different sound for the "normal" beats.

The hardware for the second embodiment does not have to be changed from the first embodiment. The user interface could be modified to include sensitivity controls, such as a potentiometer, which establish how "different" the parameters of a QRS complex must be from the baseline complexes in order to declare that an abnormal beat has been identified. Alternatively, this information could be entered via a keyboard after the specific parameters are prompted from a video monitor.

Figure 8:
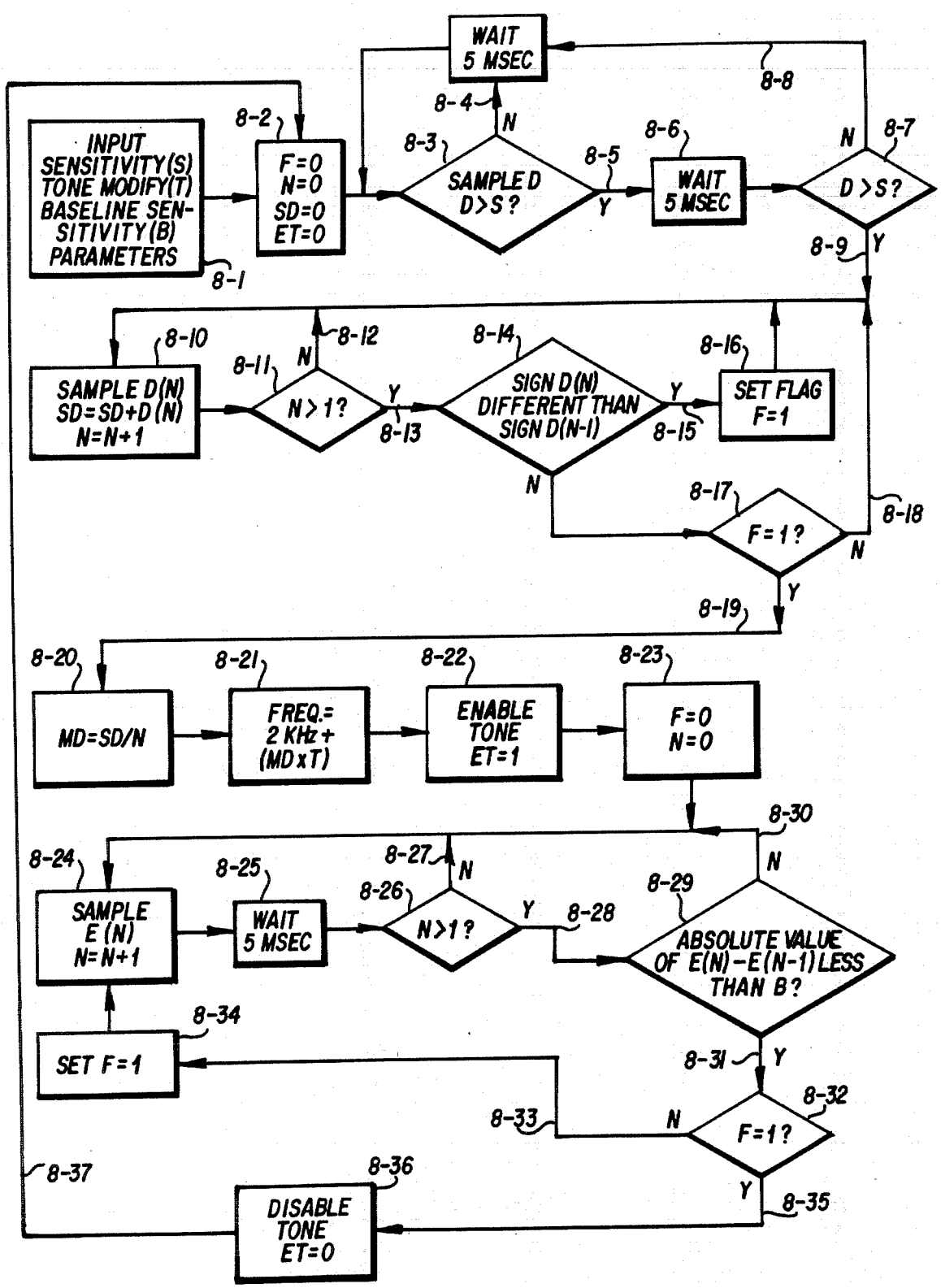
FIG. 8 is a flowchart of the software for the first embodiment.

The software for the second embodiment contains those elements already described and depicted in FIG. 8. A description of the additional software follows.

Figure 9D:
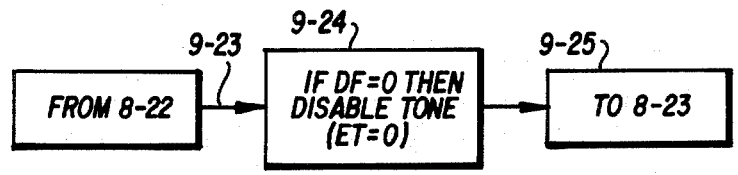
FIG. 9d is a flowchart of the sequence to suppress sound production of "normal" beats.

An algorithm for determining from the use of the system what degree of variation from the normal beat parameters is required to identify an abnormal beat is added to the beginning of the program, before 8-1 (FIG. 9a). An algorithm for determining the magnitude (M) and the mean value of D (MD) from a series of baseline normal beats is interposed between 8-1 and 8-2 (FIG. 9b). An algorithm to test if a new beat is significantly different from the baseline beats is interposed between 8-20 and 8-21 (FIG. 9c. If the beat is declared "normal" a command to disable the tone is interposed between 8-22 and 8-23 (FIG. 9d), or alternatively 8-22 may be modified to prevent enabling from taking place. These new elements will now be described in detail and are depicted in FIGS. 9.

At the beginning of the algorithm, the user is interrogated (FIG. 9a) to determine the percent variation in magnitude (VM) and the percent variation in the mean value of D (VDM) which will be required to declare that a beat is significantly different from the baseline (9-1). This information could also be determined from the position of a resistive-type device such as a potentiometer. Control then passes (9-2) to 8-1.

To establish the baseline parameters (FIG. 9b) control passes (9-3) from 8-1 to 9-4 where a counter X, the sum of the mean values of D (SMD) and the sum of the EKG peak magnitudes (SM) are all initialized to zero. Then, sequence 8-2 through 8-20 is executed (9-5) to identify a QRS complex and determine MD. Then the peak magnitude (M) is set equal to the current value of E (9-6). Then, SMD is incremented by MD, SM is incremented by M, and the counter X is incremented by 1 (9-7). Then, the counter X is tested to determine if it has exceeded the number selected for averaging purposes, in this case, arbitrarily shown to be 10 (9-S). If X is not greater than 10, then control passes back to 9-5 to capture another cycle. If X is greater than 10 (9-10), then the average baseline value of MD is determined as SMD/X and is referred to as BMD and the average baseline value of M is determined to be SM/X (9-11). Then control passes (9-12) back to 8-2. The user can reestablish these baseline parameters by stopping and restarting the system. Alternatively, it will be clear that a means could be provided to interrupt the operation of the system at any point to allow the user to reestablish such baseline measurements.

FIG. 9c discloses an algorithm to determine if the most recent captured complex differs significantly from the baseline. Control passes (9-13) from 8-20 to 9-14, where a flag to indicate that a significant difference has occurred (DF) is initiated to zero, and the peak magnitude (M) is sampled as the current value of E. Then, control passes to 9-15, where a test is conducted to determine if a significant difference in MD is detected. This is done by determining if the absolute value of 100(BMD-MD)/BMD exceeds VMD. If not (9-16), the same type of determination is made to see if a significant difference in M is detected (9-17). This is done by determining if the absolute value of 100 (BM-M)/BM exceeds VM. If not (9-18), control passes back to 8-21 with DF still equal to zero. If either of these determinations detects a significant difference (9-19 or 9-20) then DF is set to 1 (9-21) and control passes (9-22) back to 8-21 where the tone generation sequence commences.

In this specific embodiment, determining that the beat is normal will suppress tone generation. This is accomplished as shown in FIG. 9d. Control passes (9-23) from 8-22 to 9-24 where DF is tested to see if it is zero. If it is, the tone is disabled by setting ET=0. Control then passes to 8-23 and the cycle is completed as previously described for the first embodiment.

A third embodiment of the invention will now be discussed. In this embodiment, the method is similar to that in the first embodiment. However, once the tone is enabled, its frequency is continuously modulated by the amplitude of the EKG signal.

Turning now to FIG. 7, for the third embodiment, the hardware from the first embodiment is simply modified by eliminating the D/A channel 7-7, and instead, deriving the input to the voltage to frequency converter (7-9) directly from the EKG input added to an offset voltage (the offset voltage determines the center frequency).

Turning now to FIG. 8, for the third embodiment, the software from the first embodiment is modified simply by eliminating 8-20 and 8-21, thus passing control directly from 8-19 to 8-22. Also, computing SD in step 8-10 is now superfluous and may be eliminated.

A fourth embodiment will now be discussed. If the output of the EKG signal is used to modulate the frequency of the output tone on a continuous basis, a continuous modulated whining sound as is used in a Cardio-Beeper telephone transmission device would occur. This would be unacceptable for monitoring purposes as was noted above. To eliminate the the continuous whine, a very sharp notch filter centered at the frequency which corresponds to baseline input from the EKG could be employed. Thus, sounds would only be produced when the signal departs from the baseline.

Figure 10:
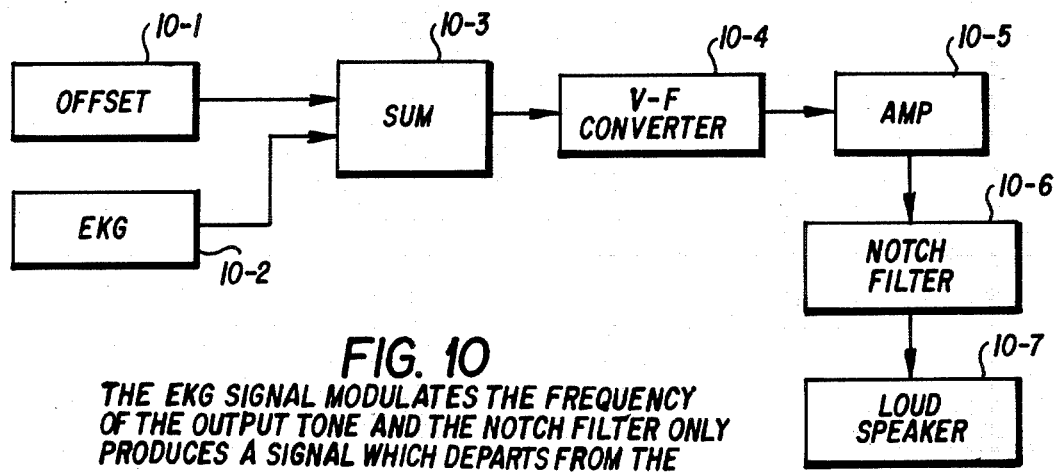
FIG. 10 is a schematic diagram of alternate system hardware wherein the EKG signal is used to modulate the frequency of the output tone.

Referring now to FIG. 10, an EKG signal is generated (10-2) and transmitted, along with an offset signal (10-1). These signals are summed (10-3) and fed to a voltage to frequency converter (10-4). The output of the converter is transmitted to an amplifier (10-5) and then in turn to a notch filter (10-6) which passes only a signal which departs from a baseline. The output of the filter is fed to a loudspeaker (10-7).

It should be apparent to one skilled in the art that combinations of the second and third embodiments can also be developed. For example, the continuous tone feature of the third embodiment could be used for all "abnormal" beats, and a conventional high pitched "beep" could be used for all "normal" beats.

I claim:

1. A cardiac diagnostic system for producing sounds from electrocardiogram signals comprising:
   an electrocardiogram (EKG) module transmitting a first signal proportional to the shape of the electrocardiogram;
   a means to receive said first signal and provide a second signal proportional to the first derivative of the first signal;
   a computing means responsive to at least one of said first and second signals identifying when a QRS complex deflection of a heartbeat has occurred, determining at least one mathematical parameter derived from the shape of said QRS complex deflection and transmitting an output signal proportional to said mathematical parameter; and
   a tone generating means responsive to the output signal of the computing means producing a tone whose characteristics are dependent upon said mathematical parameter of said QRS complex deflection and which tone is produced only for each QRS complex deflection.

2. A cardiac diagnostic system in accordance with claim 1 wherein said mathematical parameter is the mean EKG signal upstroke rate.

3. A cardiac diagnostic system in accordance with claim 1 wherein said mathematical parameter is a peak magnitude of said QRS complex deflection.

4. A cardiac diagnostic system in accordance with claim 1 further comprising a signal sent from the computing means to the tone generating means to disable the tone when the QRS complex deflection has terminated.

5. A cardiac diagnostic system in accordance with claim 1 further comprising:
   a means wherein a sensitivity range parameter distinguishing normal from abnormal heartbeats is provided within the computing means; and
   said computing means extracting parameters characterizing normal heartbeat signals and comparing the parameters extracted from the normal heartbeats with the same parameters extracted from ongoing heartbeats and generating a third signal preventing the tone generating means from generating a tone when the difference between the parameters from the normal heartbeat signals and the ongoing heartbeat signals exceeds the sensitivity range parameter.

6. A cardiac diagnostic system in accordance with claim 1 further comprising a means to provide said tone generating means with a modulating signal proportional to a or a function of said first or second signals, which modulating signal controls the frequency of said tone produced by said tone generating means to modulate about a center frequency as a function of the amplitude of said first or second signals.

7. A cardiac diagnostic system for producing sounds from electrocardiogram signals comprising:
   an electrocardiogram (EKG) module transmitting a first signal proportional to the shape of the electrocardiogram waveform;
   a tone generating means responsive to the output of the EKG module producing a tone whose characteristics are dependent upon a mathematical parameter of a QRS complex deflection and which tone is produced only for each QRS complex deflection.

8. A cardiac diagnostic system in accordance with claim 1 wherein the tone generating means responsive to an output signal of the computing means produces a tone whose time duration is dependent upon said mathematical parameter of said QRS complex deflection.

9. A cardiac diagnostic system for producing sounds from electrocardiogram signals comprising:
   an electrocardiogram (EKG) module transmitting a first signal proportional to the shape of the electrocardiogram waveform;
   a tone generating means responsive to the output of the EKG module for producing a tone whose characteristics are dependent upon a mathematical parameter of a QRS complex deflection and which tone is produced only for each QRS complex deflection; and
   means to provide said tone generating means with a second signal which causes the tone to modulate about a center frequency so that said tone produced by said tone generating means is modulated as a function of the amplitude of said first signal.

10. A cardiac diagnostic system for producing sounds from electrocardiogram signals comprising:
    an electrocardiogram (EKG) module transmitting a first signal proportional to the shape of the electrocardiogram waveform;
    a computing means responsive to said first signal identifying when a QRS complex deflection of a heartbeat has occurred, determining at least one mathematical parameter derived from the shape of said QRS complex deflection and transmitting an output signal proportional to said mathematical parameter; and
    a tone generating means responsive to the output of the computing means producing a tone whose characteristics are dependent upon a mathematical parameter of a QRS complex deflection and which tone is produced only for each QRS complex deflection.

11. A cardiac diagnostic system in accordance with claim 10 wherein said mathematical parameter is a mean EKG upstroke rate.

12. A cardiac diagnostic system in accordance with claim 10 wherein said mathematical parameter is a peak magnitude of said QRS deflection.

13. A cardiac diagnostic system in accordance with claim 10 further comprising a signal sent from the computing means to the tone generating means to disable the tone when the QRS complex deflection has terminated.

14. A cardiac diagnostic system in accordance with claim 10 further comprising:
    a means wherein a sensitivity range parameter distinguishing normal from abnormal heartbeats is provided within the computing means; and said computing means extracting parameters characterizing normal heartbeat signals and comparing the parameters extracted from the normal heartbeats with the same parameters extracted from ongoing heartbeats and generating a second signal preventing the tone generating means from generating a tone when the difference between the parameters from the normal heartbeat signals and the ongoing heartbeat signals exceeds the sensitivity range parameter.

15. A cardiac diagnostic system in accordance with claim 10 further comprising a means to provide said tone generating means with a modulating signal which causes the tone to modulate about a center frequency so that said tone produced by said tone generating means is modulated as a function of the amplitude of said first signal.

16. A cardiac diagnostic system in accordance with claim 10 wherein the tone generating means responsive to an output signal of the computing means produces a tone whose time duration is dependent upon said mathematical parameter of said QRS complex deflection.

17. A cardiac diagnostic system in accordance with claim 7 further comprising a means to receive said first signal and provide a second signal proportional to the first derivative of the first signal and wherein said tone generating means is responsive to the output of the EKG module and said means providing said second signal.

* * * * *